US008262607B2

(12) United States Patent
Porter

(10) Patent No.: US 8,262,607 B2
(45) Date of Patent: Sep. 11, 2012

(54) LIQUID EMBOLIC COMPOSITION DELIVERY DEVICES AND METHODS

(75) Inventor: Stephen Christopher Porter, Fremont, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 69 days.

(21) Appl. No.: 12/827,301

(22) Filed: Jun. 30, 2010

(65) Prior Publication Data

US 2010/0268158 A1 Oct. 21, 2010

Related U.S. Application Data

(62) Division of application No. 10/150,456, filed on May 17, 2002.

(51) Int. Cl.
*A61M 37/00* (2006.01)

(52) U.S. Cl. .......................................... 604/82; 604/83

(58) Field of Classification Search ............... 128/214.4; 604/83–92, 164.01–164.13, 523
See application file for complete search history.

(56) References Cited

U.S. PATENT DOCUMENTS

| | | | |
|---|---|---|---|
| 4,318,402 A * | 3/1982 | Vaillancourt | ............... 604/523 |
| 4,538,920 A | 9/1985 | Drake | |
| 4,819,637 A | 4/1989 | Dormandy et al. | |
| 5,156,596 A | 10/1992 | Balbierz et al. | |
| 5,443,454 A | 8/1995 | Tanabe et al. | |
| 5,681,296 A | 10/1997 | Ishida | |
| 5,785,679 A | 7/1998 | Abolfathi et al. | |
| 5,833,652 A | 11/1998 | Preissman et al. | |
| 6,139,520 A * | 10/2000 | McCrory et al. | ............... 604/60 |
| 6,146,373 A * | 11/2000 | Cragg et al. | ................. 604/523 |
| 6,152,943 A | 11/2000 | Sawhney | |
| 6,161,547 A | 12/2000 | Barbut | |
| 6,231,573 B1 * | 5/2001 | Amor et al. | ................... 606/49 |
| 6,302,898 B1 * | 10/2001 | Edwards et al. | ............. 606/214 |
| 6,626,885 B2 | 9/2003 | Massengale | |

(Continued)

FOREIGN PATENT DOCUMENTS

EP 0738520 10/1996

(Continued)

OTHER PUBLICATIONS

Communication pursuant to Article 94(3) EPC for EP application No. 03724472.0, mailed Feb. 7, 2012, 5 pages.

(Continued)

*Primary Examiner* — Theodore Stigell
*Assistant Examiner* — Gerald Landry, II
(74) *Attorney, Agent, or Firm* — Vista IP Lawgroup LLP

(57) ABSTRACT

Devices and methods are provided for delivering fluid components of an embolic mass into a body cavity. A connector, which includes a receiving element, a first port, and a second port, is provided for securing an outer tubular element and an inner tubular element such that the outer tubular element coaxially surrounds the inner tubular element. The first port is in fluid communication with the lumen of the outer tubular element when the outer tubular element is secured to the receiving element; and the second port is in fluid communication with the lumen of the inner tubular element when the inner tubular element is secured to the connector. First and second fluid components of an embolic composition are delivered into the first and second ports of the connector and through the lumens of the outer and inner tubular elements for occlusion of the body cavity.

25 Claims, 10 Drawing Sheets

U.S. PATENT DOCUMENTS

2002/0049410 A1* 4/2002 Noda et al. .................... 604/113

FOREIGN PATENT DOCUMENTS

| JP | 2001104487 | 4/2001 |
|---|---|---|
| WO | WO 01/15608 | 3/2001 |
| WO | WO 02/34323 | 5/2002 |

OTHER PUBLICATIONS

Response to Communication pursuant to Article 94(3) EPC for EP application No. 03724472.0 dated Jan. 21, 2011, response submitted Apr. 27, 2011, 13 pages.

Communication pursuant to Article 94(3) EPC for EP application No. 03724472.0 dated Jan. 21, 2011, 3 pages.

Response to Communication pursuant to Article 94(3) EPC for EP application No. 03724472.0 dated Aug. 19, 2009, response submitted on Feb. 24, 2010, 9 pages.

Communication pursuant to Article 94(3) EPC for EP application No. 03724472.0 dated Aug. 19, 2009, 5 pages.

Office action for JP application No. 2004-506892 dated Mar. 10, 2009, and translation provided by foreign associates, 4 pages.

PCT Notification of the International Search Report or the Declaration for application No. PCT/US03/14164, mailed Sep. 9, 2003, including Forms PCT/ISA/210 and 220, 8 pages.

\* cited by examiner

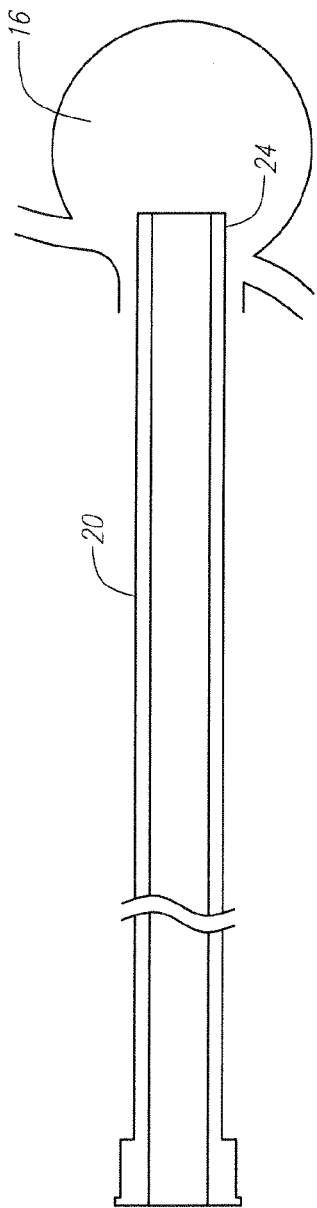
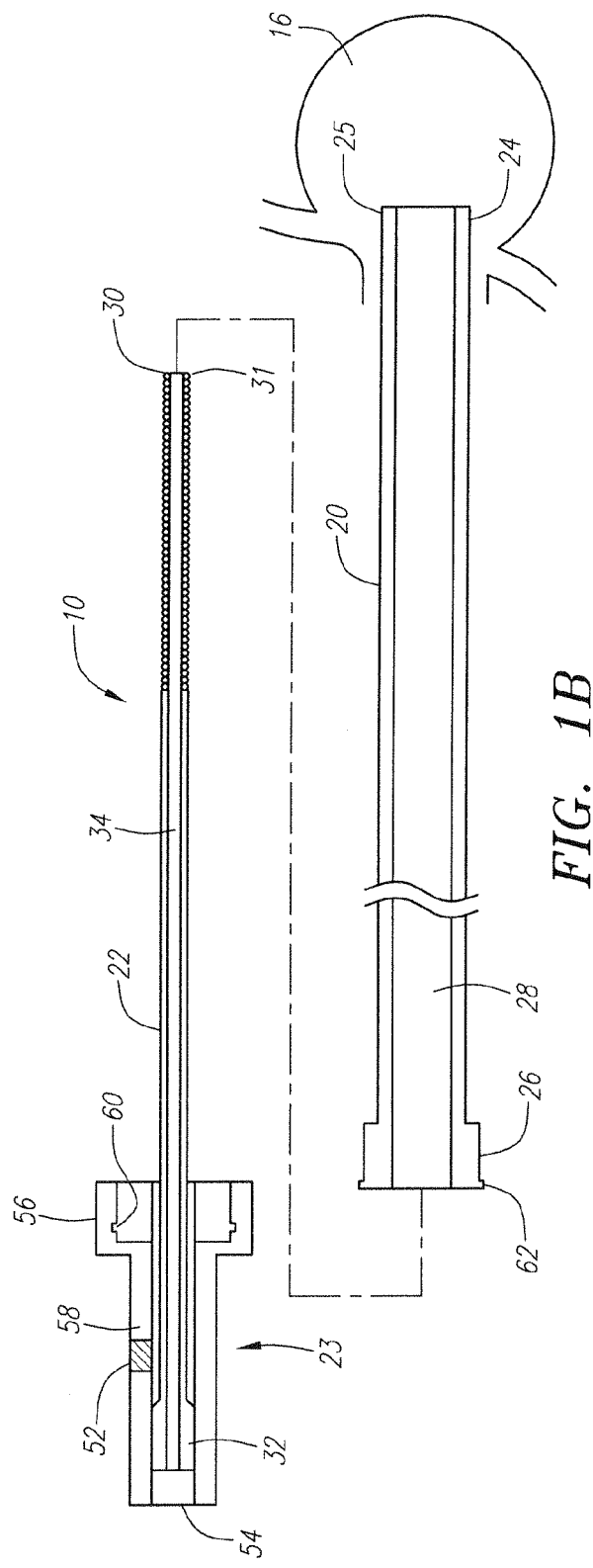
FIG. 1A
FIG. 1B

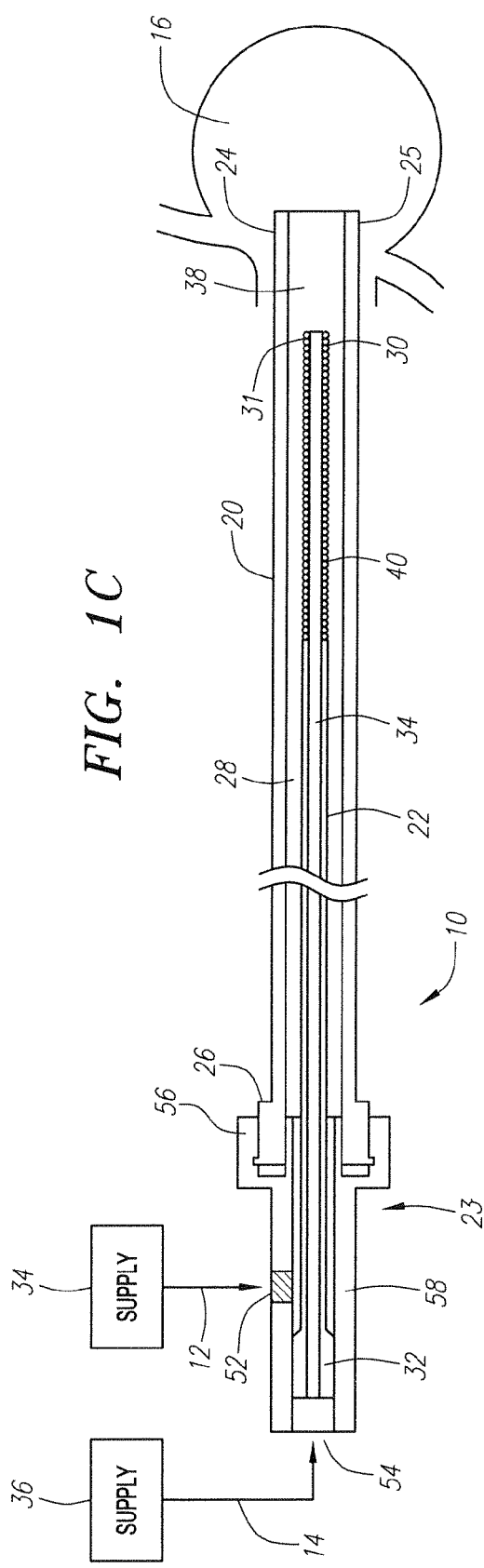
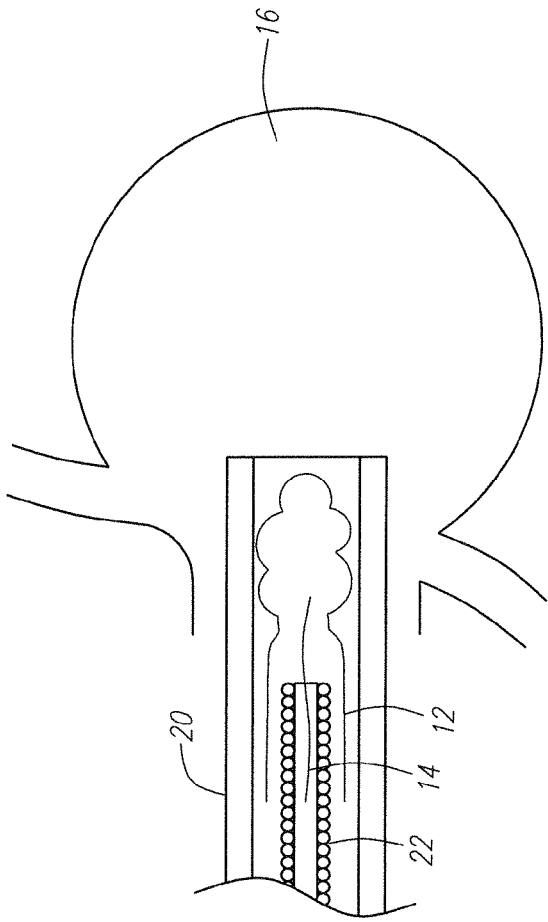
FIG. 1C
FIG. 1D

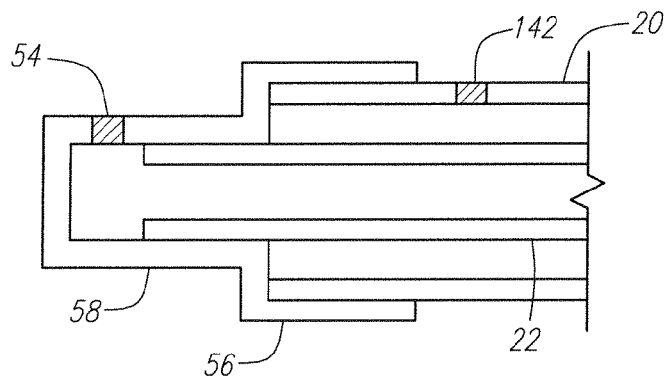
FIG. 5E
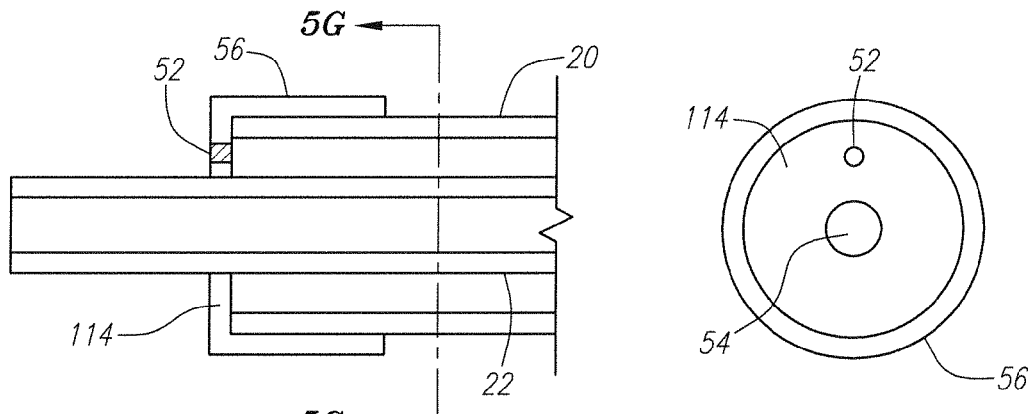
FIG. 5F
FIG. 5G
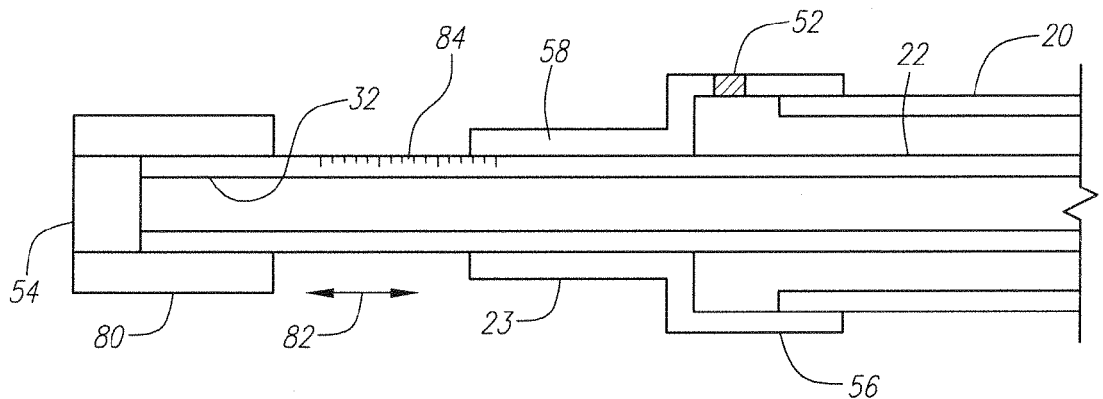
FIG. 6

LIQUID EMBOLIC COMPOSITION DELIVERY DEVICES AND METHODS

RELATED APPLICATIONS

This application is a divisional of co-pending U.S. patent application Ser. No. 10/150,456, filed May 17, 2002, which is incorporated by reference in its entirety herein.

BACKGROUND OF THE INVENTION

1. Field of the Invention

The field of the invention relates to embolic composition delivery devices, and, more particularly, delivery devices for delivering fluid components of an embolic composition.

2. Background of the Invention

In many clinical situations, blood vessels are occluded for a variety of purposes, such as to control bleeding, to prevent blood supply to tumors, or to a diseased blood vessel, such as an arteriovenous malformation (AVM), an arteriovenous fistula, or an aneurysm.

Embolization of blood vessels is particular useful in treating aneurysms. Aneurysms are abnormal blood filled dilations of a blood vessel wall, which may rupture causing significant bleeding. For the cases of intracranial aneurysms, the significant bleeding may lead to damage to surrounding brain tissue or death. Intracranial aneurysms may be difficult to treat when they are formed in remote cerebral blood vessels, which are very difficult to access. If left untreated, hemodynamic forces of normal pulsatile blood flow can rupture fragile tissue in the area of the aneurysm causing a stroke.

Traditionally, intracranial aneurysms have been surgically clipped to reduce the risk of rupture by placing a metal clip around the neck of the aneurysm to cut off and prevent further blood flow to the aneurysm. However, many aneurysms cannot be treated surgically because of either the location and configuration of the aneurysm or because the condition of the patient does not permit cranial surgery.

In another type of treatment, coils are implanted in the body of a patient in an attempt to occlude blood flow to the aneurysm. However, this procedure is time consuming because it often requires bi-plane X-rays after placement of each coil. In addition, the proper size for the coils normally needs to be determined and selected prior to implantation. Also, coils may compact over time, leaving cavities for subsequent growth of the aneurysm.

When the neck of an aneurysm is large, the foregoing methods of treatment of the aneurysm become more difficult, because the neck may have a shape that cannot be completely clipped and the coils may tend to become dislodged from the aneurysm. One aneurysm treatment procedure addressing the problems associated with surgical clipping and coil techniques involves the endovascular injection of a liquid embolic composition that solidifies in and occludes the aneurysm. The liquid embolic composition may include two liquid components that are delivered from separate sources to the aneurysm. Upon contact with each other, the liquid components react and solidify into an embolic mass, thereby occluding the aneurysm. Examples of liquid embolic compositions are described in U.S. Pat. Nos. 6,139,520 and 6,152,943, the entireties of which are expressly incorporated herein by reference. U.S. Pat. No. 6,139,520 discloses a cross linked polysaccharide fiber formed by combining a first liquid including polysaccharide and a second liquid including an ionic cross linking agent. U.S. Pat. No. 6,152,943 discloses a polymer formed by two components.

The delivery of liquid embolic composition to intracranial spaces requires the use of catheters that are relatively soft and flexible in order to navigate to the desired locations. Existing liquid embolic delivery systems that require delivery of more than one liquid component to the distal portion of the delivery catheter may be cumbersome and may have limited utility due to the need to have more than one independent lumen. In addition, delivery systems may be expensive to develop and manufacture due to the need to fabricate multiple components that are specifically required for the systems. Furthermore, when more than one liquid component is delivered to an aneurysm, there is a risk that the liquid components may not be completely combined within the aneurysm to form the desired embolic composition. As the result, the unmixed portion of either one of the liquid components may dissipate into the blood stream or travel to other locations within the body.

In light of the foregoing, it would be advantageous to have improved devices and methods for delivering and combining fluid components of an embolic composition.

SUMMARY OF THE INVENTION

The present invention is directed to devices and methods for delivering embolic mass to a body cavity, and, more particularly, devices and methods for delivering fluid components of an embolic composition to form an embolic mass for occlusion of a body cavity.

According to one aspect of the present invention, a device for delivering fluid components of an embolic composition includes a connector for securing an outer tubular element and an inner tubular element. The connector includes a receiving element, a first port, and a second port. The receiving element of the connector is configured for securing the proximal end of the outer tubular element. The connector may include a sleeve for securing the inner tubular element. Alternatively, if a sleeve is not used, the inner tubular element may be secured to the second port of the connector. The outer tubular element is configured for delivery of a first fluid component, e.g., a polysaccharide, while the inner tubular element is configured for delivery of a second fluid component, e.g., a cross-linking agent. The first and second ports of the connector are configured for being in fluid communication with the respective lumens of the outer and inner tubular elements when the outer and inner tubular elements are secured to the connector. The ports may be axially or transversely associated with the connector (or in communication with the connector by tubular connections) and can be located anywhere on the connector that effects fluid communication between the lumens of the inner and outer tubular elements and the first and second fluid component supplies.

According to a second aspect of the invention, a device for delivering fluid components of an embolic composition includes an outer tubular element, an inner tubular element, a connector for securing the outer and inner tubular elements, and a mixing zone that is in fluid communication with the lumens of the outer and inner tubular elements. The mixing zone is provided within the distal tip of the outer tubular element, where the first fluid component and the second fluid component are combined to form a desired embolic composition. Once the two fluid components contact each other and the desired embolic composition is formed, the embolic composition then solidifies to form an embolic mass to occlude a body cavity.

The inner tubular element can be fixably secured within the connector, or to advantageously provide relative displacement between the inner and outer tubular elements, can be slidably secured within the connector to allow adjustment of the mixing zone and facilitation of the embolic composition dispensing process. Distal displacement of the inner tubular element relative to the outer tubular element can also facilitate the dispensing of the embolic mass from the distal end of the device. If relative displacement of the inner and outer tubes is provided, radiopaque markers can be provided on the distal tips of the inner and outer elements to, for example, ensure that the desired size of the mixing zone is achieved. The inner tubular element can also advantageously have a stopper configured for limiting proximal axial displacement of the inner tubular element relative to the connector, so that, for example, the proper mixing zone size can be achieved. Even more alternatively, a marker can be placed at the proximal end of the inner tubular element. To provide ease of manipulation, a handle can be attached to the proximal end of the inner tubular element. An optional cutting element may also be provided to cut the embolic mass from the distal end of the device.

In accordance with a third aspect of the present inventions, a device for delivering fluid components of an embolic composition includes an outer tubular element, an inner tubular element, a connector for securing the outer and inner tubular elements, and a static mixing element disposed within the distal end of the outer tubular element. The static mixing facilitates the mixing of at least one of the first and second fluid components when exiting the corresponding first and second lumens into the mixing zone.

The static mixing element can take on a variety of forms, such as, e.g., a plurality of ribs that are disposed within the corresponding one of the first and second lumens to provide a turbulent or complex flow pattern with respect to the pertinent fluid component, an element disposed within the mixing zone to divert the pertinent fluid component, or a plurality of elements that project into and disrupt uniform flow of the pertinent fluid component to provide turbulent or complex flow thereof.

In accordance with a fourth aspect of the present inventions, a method of dispensing an embolic mass into a body cavity is performed. The method includes placing the distal end of an outer tubular element near or into a body cavity, and then positioning an inner tubular element within the lumen of the outer tubular element, so that a mixing zone is formed within the distal end of the outer tubular element. Alternatively, the inner tubular element can be positioned within the outer tubular element prior to placement of the distal end of the outer tubular element near or into the body cavity. The method then includes mating the proximal ends of the outer and inner tubular elements to a connector, such that the proximal ends thereof are placed into a coaxial relationship with each other. If the outer tubular element is placed into the patient's body prior to positioning the inner tubular element within the outer tubular element, the proximal end of the inner tubular element can be mated with the connector prior to such positioning, and the outer tubular element can be mated with the connector after the positioning.

The first and second fluids are then delivered to the mixing zone through the respective lumens of the outer and inner tubular elements, mixed within the mixing zone to form the embolic composition, and then dispensed into the body cavity, such as, for example, using a fluid pressure or advancing the distal tip of the inner tubular element towards the distal tip of the outer tubular element. Although the body cavity should not be so limited, the invention particularly lends itself to the treatment of aneurysms, AVMs, and tumors.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 1A-1D illustrate steps of using the catheter device in FIG. 1;

FIGS. 5A-5G illustrate partial cross-section side views of various alternative configurations for the connector of the FIG. 1 device;

FIG. 6 illustrates a partial cross-sectional side view of an alternative delivery device to the FIG. 1 device, wherein the inner tubular element can be axially translated relative to the outer tubular element;

DETAILED DESCRIPTION OF THE PREFERRED EMBODIMENTS

Figure 1:
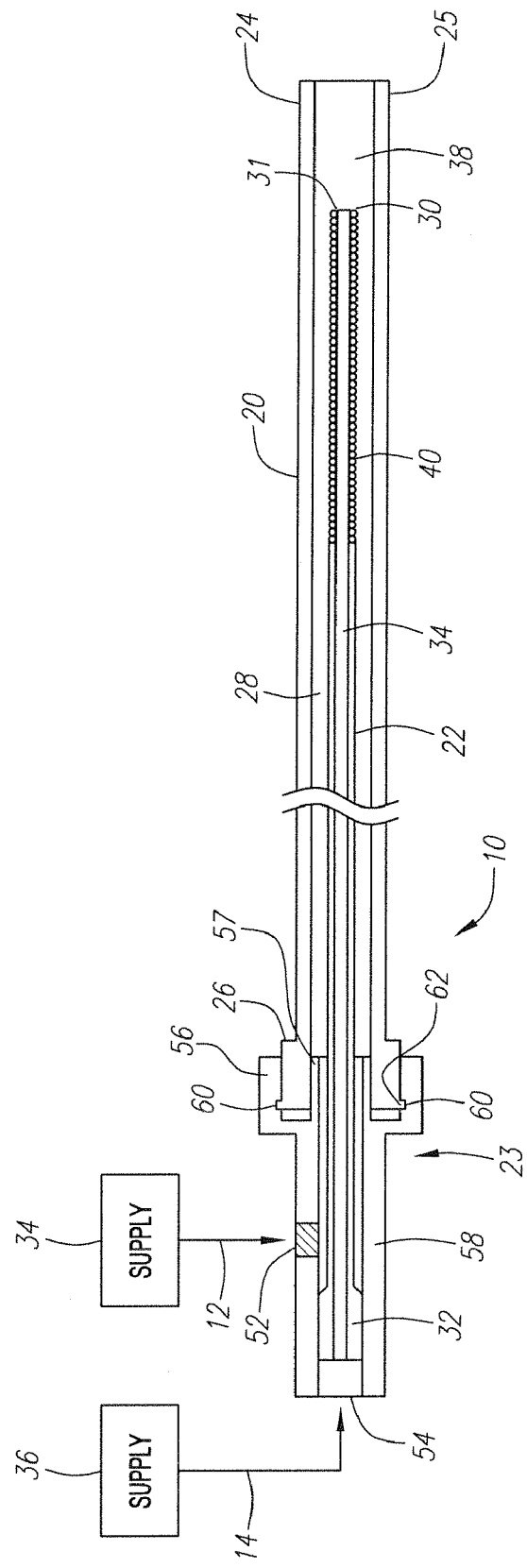
FIG. 1 is a cross-sectional side view of a catheter device for delivering fluid components of an embolic composition, particularly showing a connector in accordance with a preferred embodiment of the present invention.

Referring to FIG. 1, a catheter device 10 for delivering a first fluid component 12 and a second fluid component 14 of an embolic composition is described. The catheter device 10 includes a connector 23 that is in accordance with a preferred embodiment of the present invention, an outer tubular element 20, and an inner tubular element 22. The connector 23 is for securing an outer tubular element 20 and an inner tubular element 22 such that the outer tubular element 20 coaxially surrounds the inner tubular element 22. The outer tubular element 20 has a distal end 24, a proximal end 26, and a lumen 28. Similarly, the inner tubular element 22 has a distal end 30, a proximal end 32, and a lumen 34. The connector 23 includes a transversely situated first port 52, an axially situated second port 54, a receiving element 56, and a sleeve 58. The connector 23 is designed to be connected to a first supply 34 and a second supply 36, which contain the first fluid component 12 and the second fluid component 14, respectively. Either of supplies 34 and 36, for example, may be a syringe, a tank, or a pump. Each of the supplies 34 and 36 may also be a part of a dual barrel syringe.

As shown in FIG. 1, the receiving element 56 of the connector 23 is for securing the outer tubular element 20, such that the first port 52 is in fluid communication with the lumen 28 of the outer tubular element 20, and could direct flow of the first fluid component 12 to within the lumen 28 of the outer tubular element 20. Similarly, the sleeve 58 of the connector 23 is for securing the inner tubular element 22, such that the second port 54 is in fluid communication with the lumen 34 of the inner tubular element 22, and could direct flow of the second fluid component 14 to within the lumen 34 of the inner tubular element 22. As such, the connector 23 acts as an interfacing mechanism for delivery of the first fluid component 12 from the supply 34 and the second fluid component 14 from the supply 36, to the lumen 28 of the outer tubular element 20 and the lumen 34 of the inner tubular element 22, respectively. The connector 23 will be described in further detail below.

The outer tubular element 20 is preferably a microcatheter that is capable for use in tortuous blood vessels, such as intracranial blood vessels. The outer tubular element is preferably made of a flexible material such as plastic. However, other flexible materials may be used. Examples of the outer tubular element 20 include microcatheters available from Boston Scientific/Target, Fremont, Calif., U.S., having trademarks EXCELSIOR™1018™, EXCELSIOR™ SL-10, RENEGADE™18, and TRACKER® EXCEL™14.

The inner tubular element 22 is also preferably made of flexible materials such as plastic, so that it could bend within the lumen 28 of the outer tubular element 20. The inner tubular element 22 should also have sufficient axial strength and stiffness to prevent kinking of the inner tubular element 22 within the lumen 28 of the outer tubular element 20. Without circumferential reinforcement, the inner tubular element 22 may expand radially when the second fluid component 14 is being delivered by pressure within the lumen 34 of the inner tubular element 22, which may, in turn, lead to blockage of the annular space in which the first fluid component 12 is flowing. Therefore, the inner tubular element 22 is preferably circumferentially reinforced along its length to prevent radial expansion thereof when the second fluid component 14 is being delivered within the lumen 34 of the inner tubular element 22.

Figure 2:
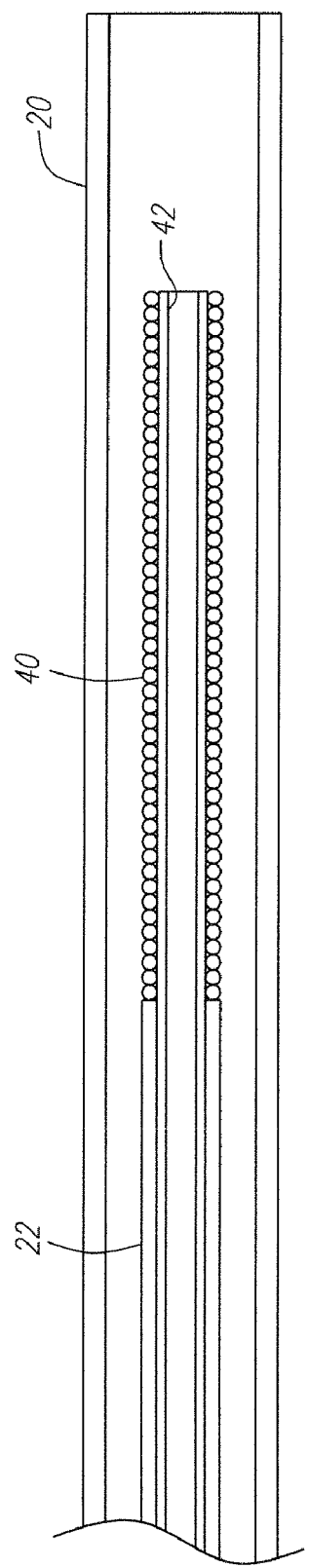
FIG. 2 is a partial cross-sectional side view of the distal end of the device shown in FIG. 1, particularly showing a preferred reinforcement configuration for an inner tubular element used in the FIG. 1 device.
Figure 3:
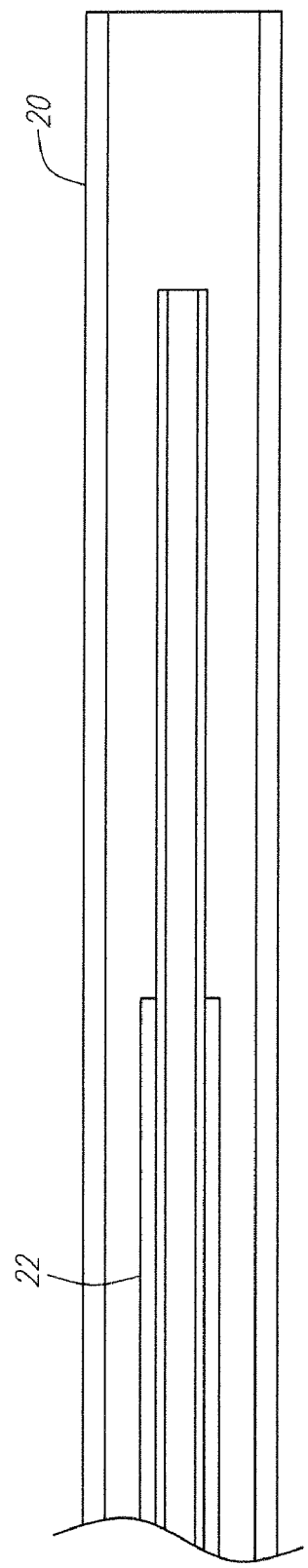
FIG. 3 is a partial cross-sectional side view of the distal end of the device shown in FIG. 1, particularly showing another preferred reinforcement configuration for an inner tubular element used in the FIG. 1 device.

As shown in FIGS. 1 and 2, the inner tubular element 22 preferably has a flexible portion 40 near the distal end 30. The flexible portion 40 of the inner tubular element 22 is preferably a helical coil or a braided element Alternatively, the flexible portion 40 of the inner tubular element 22 may be constructed by laser-cutting a separate tubular element in a spiral configuration to form a coil-like structure. An inner layer of material 42, such as Teflon, may run along the entire length of the inner tubular element 22 to contain the second fluid component 14 within the inner tubular element 22. An outer laminate (not shown) may also be used to cover the inner tubular element 22 (including the flexible portion 40), and the stiffness along the length of the inner tubular element 22 may be varied by the material and/or thickness of the laminate. The extent of the flexible distal portion 40 of the inner tubular element 22 is preferably at least 5 to 30 centimeters from the tip 31 of the proximal end 30. However, the flexible portion 40 may also extend along the entire length of the device, and the stiffness along the length of the inner tubular element 22 may be varied, for example, by changing the frequency of the helical windings of the coil. Alternatively, as shown in FIG. 3, the stiffness along the length of the inner tubular element 22 may also be varied by changing the thickness of the inner tubular element 22.

The outer tubular element 20 and the inner tubular element 22 are preferably circular in cross-section. Alternatively, the cross-section of either of the outer tubular element 20 and the inner tubular element 22 may have other shapes such as oval, square, triangle, or an irregular geometry. The inner diameter of the outer tubular element 20 is preferably about 0.02 inch. However, other sizes of the outer tubular element 20 may be used. The inner diameter of the outer tubular element 20 should be selected so as to allow ease of flow of the first fluid component 12 within the lumen 28 outside the inner tubular element 22. The inner diameter of the inner tubular element 22 is preferably between 0.005 to 0.012 inch, and the outer diameter of the inner tubular element 22 is preferably between 0.01 to 0.15 inch. However, other dimensions of the inner and outer diameters of the inner tubular element 22 may also be used. The inner diameter of the inner tubular element 22 should be selected to allow ease of flow of the second fluid component 14 within the lumen 34.

Figure 4A:
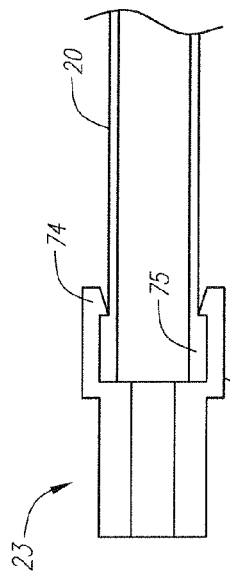
FIG. 4A illustrates partial cross-sectional side view of a preferred embodiment for securing an outer tubular element of the FIG. 1 device to the connector.

Referring now to the connector 23 in FIG. 1, the receiving element 56 of the connector 23 includes a securing mechanism for detachably securing the proximal end 26 of the outer tubular element 20 to the connector 23. In particular, the receiving element 56 includes an annular indentation 60 for mating with an annular ridge 62 of the outer tubular element 20, thereby securing the outer tubular element 20 to the connector 23. The connector 23 may also optionally include a backing sleeve 57 disposed on the distal end of the sleeve 58, such that the proximal end 26 of the outer tubular element 20 can be mated with the connector 23 by advancing it into the annular space formed by the receiving element 56 and the backing sleeve 57. The backing sleeve 57 provides additional stiffness to the receiving element 56 and helps secure the proximal end 26 of the outer tubular element 20 to the connector 23. FIG. 4A shows a variation of the connector 23 of FIG. 1, which includes a threaded Luer-Loc type system. Such a connector is preferred because it allows ease of attachment and detachment of the outer tubular element 20, and it may be used with a wide variety of existing microcatheters. It should be noted that the receiving element 56 is preferably designed to mate with a proximal end of a currently marketed microcatheter. This has the benefit of reducing the overall cost of development by not having to manufacture the outer tubular element.

Figure 4B:
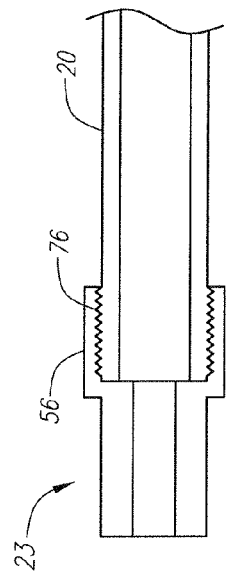
FIGS. 4B-4F illustrate partial cross-sectional side views of various alternative embodiments for securing an outer tubular element of the FIG. 1 device to the connector.
Figure 4C:
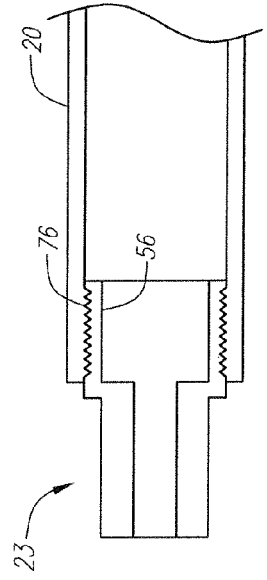
Figure 4D:
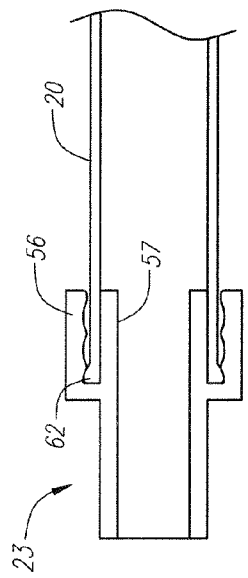
Figure 4E:
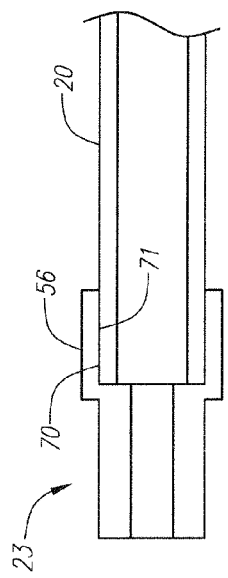
Figure 4F:
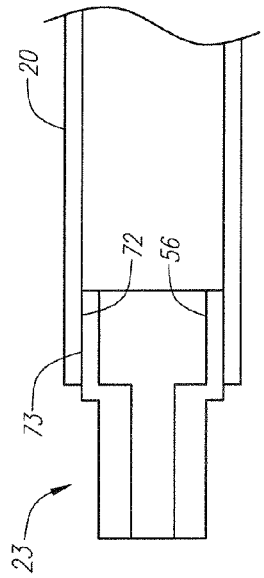

FIGS. 4B to 4F illustrate examples of alternative securing mechanisms, which may be used for securing the outer tubular element 20 to the connector 23. The inner tubular element 22 and the first port 52 are not shown in FIGS. 4B to 4F for purpose of clarity. In FIG. 4B, the outer tubular element 20 is secured to the receiving element 56 of the connector 23 by bearing and/or frictional force between an exterior surface 70 of the outer tubular element 20 and an interior surface 71 of the receiving element 56. In FIG. 4C, the outer tubular element 20 is secured to the receiving element 56 of the connector 23 by bearing and/or frictional force between an interior surface 72 of the outer tubular element 20 and an exterior surface 73 of the receiving element 56. FIG. 4D illustrates a locking mechanism 74 at the interior surface of the receiving element 56 for mating an enlarged portion 75 of the outer tubular element 20. FIGS. 4E and 4F show that the outer tubular element 20 may be detachably connected to the connector 23 by screw-type connection 76. Other mechanisms for securing a tubular element to a port, as are known in the art, may be used.

As shown in FIG. 1, the sleeve 58 of the connector 23 is configured for receiving and securing the proximal end 32 of the inner tubular element 22 to the connector 23, such that the proximal end 32 of the inner tubular element 22 is coaxially surrounded by the proximal end 26 of the outer tubular element 20 within the connector 23. The inner tubular element 22 is preferably rigidly secured to the sleeve 58 using the previously described configurations used for securing the outer tubular element 20 to the receiving element 56. The inner tubular element 22 may also be fabricated together with the connector 23 as one component.

Because the connector 23 maintains the proximal ends of the outer and inner tubular elements 20 and 22 in a coaxial relationship, the first fluid component 12 is delivered through the transversely situated first port 52 to within the lumen 28 of the outer tubular element 20, but outside the inner tubular element 22. The diameter and shape of the first port 52 may be selected to mate with an element, such as a tubular element or a valve for examples, of the first supply 34 that contains the first fluid component 12.

FIG. 1 shows that the second port 54 of the connector 23 is defined by the opened-end of the sleeve 58 at the proximal end of the sleeve 58. Like the first port 52, the diameter and shape of the second port 54 may be selected to mate with an element, such as a tubular element or a valve for examples, of the second supply 36 that contains the second fluid component 14. As shown in FIG. 1, the proximal end 32 of the inner tubular element 22 preferably stays within the sleeve 58 of the connector 23, so that the second fluid component 14 is delivered through the axially situated second port 54 to within the lumen 34 of the inner tubular element 22. Alternatively, the proximal end of the inner tubular element 22 may extend outside the proximal end of the sleeve 58, as will be explained below with reference to FIG. 6.

It should be noted that the connector 23 shown in FIG. 1 is just one example of maintaining fluid communications with the respective lumens of the outer and inner tubular elements 20 and 22. FIGS. 5A-5F illustrate examples of the alternative embodiments of the connector 23.

Figure 5A:
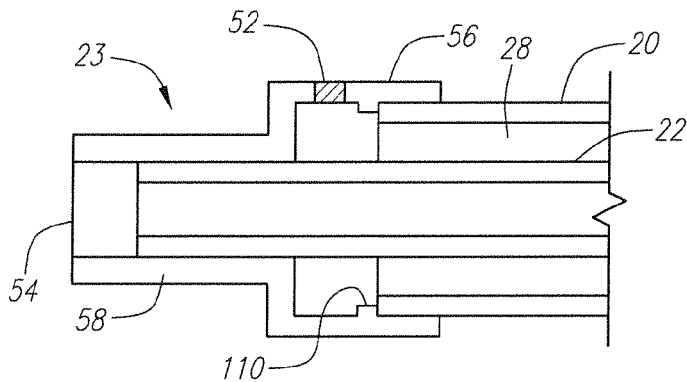
Figure 5B:
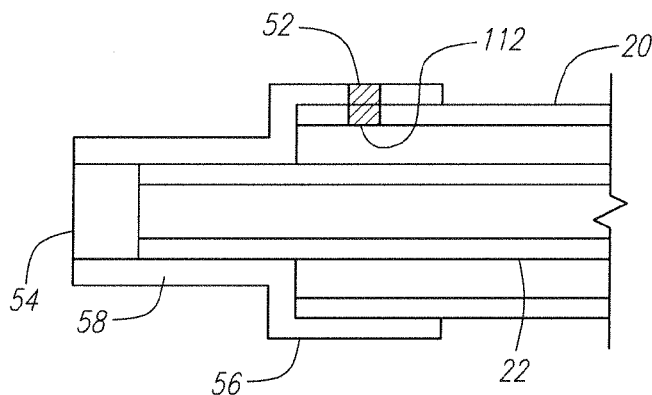

As shown in the connector 23 of FIG. 5A, the first port 52 is located along the receiving element 56 such that the first fluid component 12 delivered to the first port 52 would flow through the interior of the receiving element 56 within the lumen 28 of the outer tubular element 20 but outside the inner tubular element 22. A stopper 110 may be located along the receiving element 56 to prevent the outer tubular element 20 from advancing too far into the connector 100, and blocking the port 52. Alternatively, as shown in the connector 23 of FIG. 5B, the proximal end 24 of the outer tubular element 20 may contain an access hole 112 such that the access hole 112 would align with the first port 52 when the outer tubular element 20 is detachably secured to the receiving element 56.

Figure 5C:
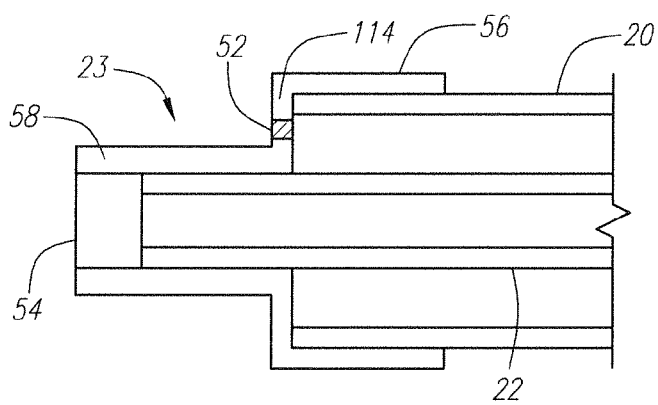
Figure 5D:
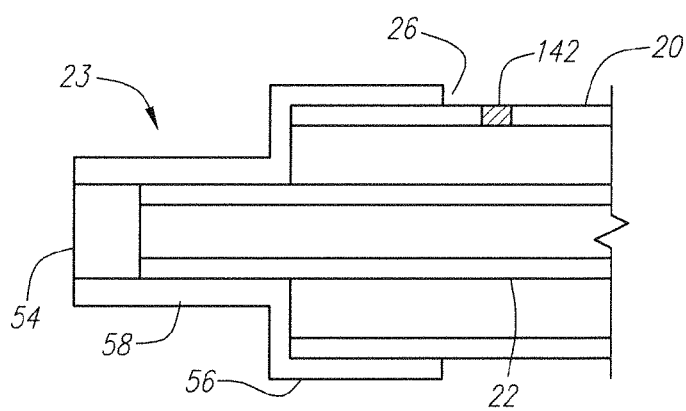

As shown in the connector 23 of FIG. 5C, the first port 52 may be located at a bend 114 defining the transition between the sleeve 58 and the receiving element 56. As shown in the connector 23 of FIG. 5D, a first port is not required. Rather, the first fluid component 12 is delivered to within the lumen 28 of the outer tubular element 20 through an opening 142 located near the proximal end 26 of the outer tubular element 20. As shown in the connector 23 of FIG. 5E, its proximal end is enclosed, and the second port 54 is transversely situated on the sleeve 58.

FIG. 5F shows a connector 23 which includes a receiving element 56 for detachably securing the proximal end of the outer tubular element 20, a first port 52, and a second port 54. Unlike the connectors shown in FIGS. 5A to 5E, the connector 23 in FIG. 5F does not require a sleeve 58. Rather, the inner tubular element 22 is secured within the second port 54 of the connector 23. The inner tubular element 22 may be detachably or slidably secured to the connector 23. Alternatively, the inner tubular element 22 may be fixedly attached, or be disposed on the connector 23, for example, during a manufacturing process of the connector 23. The proximal end of the inner tubular element 22 is configured to mate with an element, such as a tubular element or a valve for examples, of the second supply 36 that contains the second fluid component 14. The first port is preferably located at a bend 114 adjacent to the receiving element 56. Alternatively, the first port 52 may be located at the receiving element 56, as described previously. FIG. 5G is a sectional view of the connector 23 of FIG. 5F. The outer tubular element 20 and the inner tubular element 22 are not shown in FIG. 5G for clarity.

FIG. 6 shows an alternative embodiment of the connector 23, which allows the inner tubular element 22 to be longitudinally displaced relative to the outer tubular element 20. That is, the inner tubular element 22 is slidably secured to the sleeve 58, as indicated by the arrow 82, so that the inner tubular element 22 can move longitudinally relative to the connector 23, and thus, the outer tubular element 20. In this embodiment, the proximal end 32 of the inner tubular element 22 extends outside the proximal end of the sleeve 58, and is attached to a handle 80, which can be conveniently used to control the position of the inner tubular element 22 relative to the outer tubular element 20. In this case, the second port 54 can be axially situated on the handle 80 for mating with a tubular element or a valve, for examples, of the second supply 36 for delivery of the second fluid component 14 to the lumen 34 of the inner tubular element 22. Optionally, rather than employing a handle 80, the proximal end 32 of the inner tubular element 22 may be directly connected to the second supply 36. One advantage of having a connector 23 that could slidably secure the inner tubular element 23 is that the extent of a mixing zone 38, being the space between the distal tips of the inner and outer tubular elements (FIG. 1), can be varied.

The mixing zone 38 will be described in detail below. The proximal end 32 of the inner tubular element 22 may also have marker 84 to help determine the relative location of the distal tips of the two tubular elements. Additionally, the displacement of the inner tubular element 22 relative to the outer tubular element 20 may aid in discharging the mixture of the first and second fluid components 12 and 14 from the distal end 24 of the outer tubular element 20 into the body cavity, as will be described in further detail below.

The method of using the device 10 will now be discussed with reference to FIGS. 1A to 1D. When using the device 10, the proximal end 30 of the inner tubular element 22 is first secured within the sleeve 58 of the connector 23. As discussed previously, the inner tubular element 22 may be rigidly or slidably secured to the connector 23. Furthermore, if the inner tubular element 22 is fabricated or manufactured as one component with the connector 23, such a step is then unnecessary.

Next, the outer tubular element 20 is then inserted into the body of a patient, so that the distal end 24 of the outer tubular element 20 is adjacent to or within the body cavity 16 to be occluded (FIG. 1A). The insertion of the outer tubular element 20 may be facilitated by the use of a guidewire and or guiding catheter, as is known in the art. In addition, the movement of the outer tubular element 20 may be monitored fluoroscopically.

Once the outer tubular element 20 is in place, the distal end 30 of the inner tubular element 22 is then inserted into the lumen 28 at the proximal end 26 of the outer tubular element 20, and the inner tubular element 22 is advanced forward until the proximal end 26 of the outer, tubular element 20 securely engages the receiving element 56 of the connector 23 (FIG. 1B).

Alternatively, instead of inserting the outer tubular element 20 into the patient's body first, the inner tubular element 22 may first be inserted into the lumen 28 of the outer tubular element 20 before the outer tubular element 20 is inserted into a patient's body. Then both the outer tubular element 20 and the inner tubular element 22 are then inserted into the patient's body. Guidewire and/or guiding catheter may also be used to facilitate the insertion of the two tubular elements.

After both the outer tubular element 20 and the inner tubular element 22 are secured to the connector 23, the inner tubular element 22 is preferably positioned such that a distal tip 31 is proximal to a distal tip 25 of the outer tubular element 20, thereby providing a mixing zone 38 within the distal end 24 of the outer tubular element 20 and outside the distal end 30 of the inner tubular element 22. (FIGS. 1 and 1C) In particular, the mixing zone 38 is the space between the distal tip 25 of the outer tubular element 20 and the distal tip 31 of the inner tubular element 22. The mixing zone 38 allows the first fluid component 12 and the second fluid component 14 to contact and combine with each other to form into the desired embolic composition before either one of the two fluid components is discharged out of the lumen 28 of the outer tubular element 20. The length of the mixing zone 38 is preferably less than 5 centimeters, but other dimensions may be used, depending on the fluid components and/or specific application.

Figure 7:
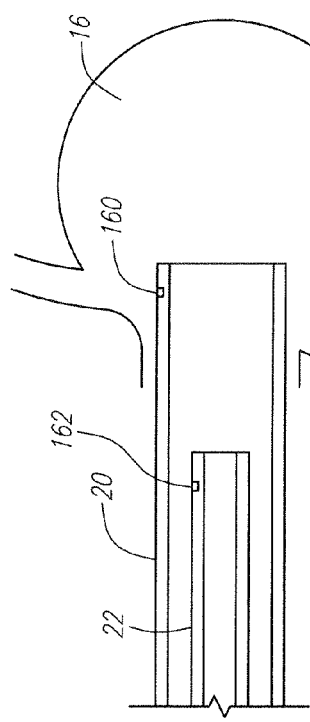
FIG. 7 illustrates a partial cross-sectional side view of the distal end of the FIG. 1 device, particularly showing the use of radiopaque markers.
Figure 8:
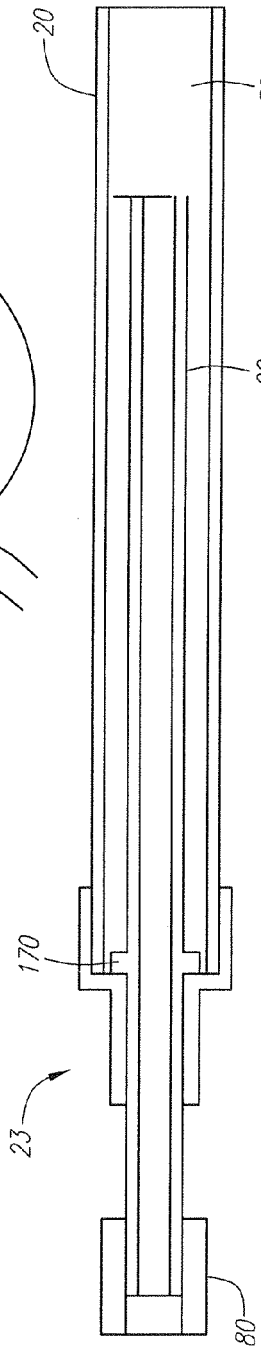
FIG. 8 illustrates a cross-sectional side view of the FIG. 6 delivery device, particularly showing a stopper to limit proximal displacement of the inner tubular element relative to the outer tubular element.
Figure 8A:
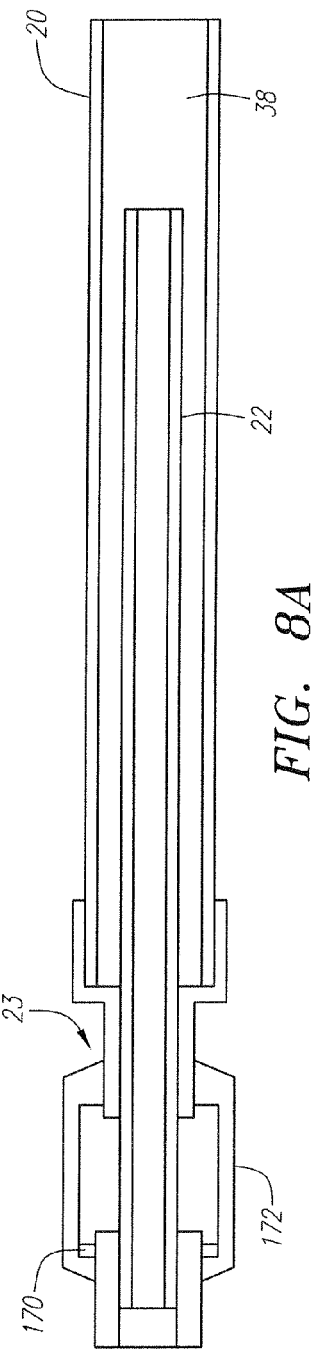
FIG. 8A illustrates a variation of the delivery device shown in FIG. 8, particularly showing the stopper being at the handle.

Various methods may be used to determine or verify the relative position of the distal ends of the two tubular elements to ensure that a desired length of the mixing zone 38 is provided. This is particularly important if the inner tubular element 22 is slidably secured to the connector 23, as described previously. As shown in FIG. 7, the distal ends 24 and 30 of the outer and inner tubular elements 20 inner tubular element 22 may have radiopaque markers 160 and 162, respectively. This allows a physician to determine the relative positions of the distal tips 25 and 31 of the two tubular elements 20 and 22, and the position of the outer tubular element 20 relative to the body cavity 16. Alternatively, as shown in FIG. 8, the inner tubular element 22 may have a stopper 170 that bears against a portion of the connector 23 when the inner tubular element 22 is retracted to a position that provides the mixing zone 38. FIG. 8A shows a variation of the device in FIG. 8, in which the stopper 170 is located at the handle 80. The connector 23 includes an extension 172 that prevents the inner tubular element 22 from sliding too far towards the proximal end of the system. Furthermore, as discussed previously, the marker 84 at the proximal end 32 of the inner tubular element 20 may also be used by a physician to determine the relative location of the distal tips 25 and 31 of the two tubular elements 20 and 22. Other known methods of locating a medical device may also be used.

Once the outer and inner tubular elements 20 and 22 are positioned at the desired location, the first fluid component 12 is then delivered through the first port 12 into the lumen 28 of the outer tubular element 20. Similarly, the second fluid component 14 is also delivered through the second port 14 into the lumen 34 of the inner tubular element 22. If injection of either of the fluid components 12 and 14 poses a potential risk to a patient, the delivery system needs to be prepared such that the first and second fluid components 12 and 14 will simultaneously be delivered into the reaction zone when delivery begins. This can be done in a one or two-step procedure. In a one-step procedure, both fluid components are injected at the same time so that they reach the reaction zone 38 simultaneously. This can be achieved if the ratio of the total volumes of the fluid components between the delivery source and the entry point of the reaction zone 38 (the volume of the lumen and the connector) is the same as the ratio of the required flow rates for the two fluid components. In particular, the respective diameters of the outer and inner tubular elements 20 and 22, the connector 23, and/or the ports 52 and 54 may be selected such that the ratio of the total volumes of the fluid components 12 and 14 corresponds with the mix-ratio of the two fluid components 12 and 14. Thus: $V_1/V_2 = Q_1/Q_2 = m$ (where $V_1$ and $V_2$ represent total volumes and $Q_1$ and $Q_2$ represent flow rates of the first and second fluid components 12 and 14, respectively; and m represents the mix ratio of the first and second fluid components 12 and 14.) A dual barreled syringe having the same or connected plunger assemblies may be used to simultaneously deliver the two fluid components to the system. In this case, fluid components having specific mix ratios may be delivered by having different barrel diameters.

Alternatively, in the two-step procedure, the first fluid component 12 may be introduced to fill the first lumen 28 to the point of the mixing zone 38 (i.e. to near the tip 31 of the inner tubular element 22), and then the second fluid 14 component may be introduced to fill the second lumen 34 to the point of the mixing zone 38 (i.e. to near the tip 31). Each of the fluid components 12 and 14 may be radiopaque so that fluoroscopic visualization may be used to monitor the progression of each fluid component. Once the system is so prepared, both fluid components 12 and 14 are then simultaneously injected into the mixing zone 38. Furthermore, in either of the one-step or two-step procedures, the first and second fluid components 12 and 14 may be delivered in alternate and successive pulse(s) to improve the homogeneity of the mixture of the two fluid components 12 and 14. For either the one-step or the two-step procedure, the delivery of the embolic composition may also be facilitated by an endoluminal device, such as a balloon catheter, stent, or stent-graft, which confines the embolic composition within a lumen and causes a temporary obstruction to the movement of the mixed fluid components 12 and 14 before the embolic composition has substantially solidified within the body cavity 16. Examples of such devices include the Sentry™ balloon catheter and the TriSpan™ coil (both from Boston Scientific/TARGET; Fremont, Calif.), and the devices disclosed in WO 99/03404 and U.S. Pat. No. 5,795,331.

The first and second fluid components 12 and 14 are delivered from the respective lumens to the mixing zone 38 within the distal end 24 of the outer tubular element 20 where the two fluid components contact and combine with each other to form a desired embolic composition. To facilitate combining the two fluid components in a more efficient manner, and to improve the homogeneity of the mixture of the two fluid components, a mixing element may be used to induce turbulent or complex flows within the mixing zone 38.

Figure 9:
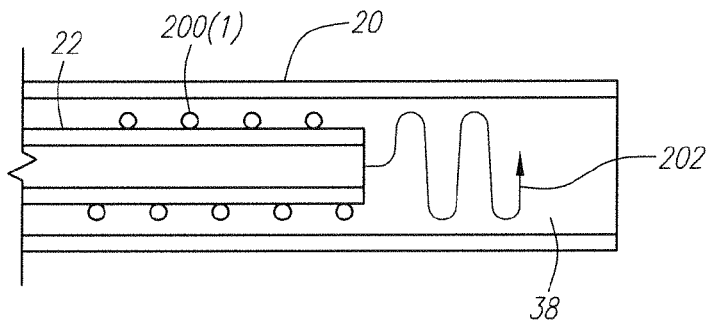
FIG. 9 is a partial cross-sectional side view of the distal end of the FIG. 1 device, particularly showing one embodiment of a static mixing element used to facilitate mixing of the fluid components within a mixing zone.
Figure 10:
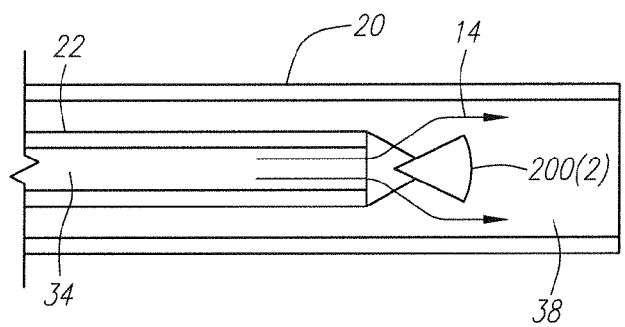
FIG. 10 is a partial cross-sectional side view of the distal end of the FIG. 1 device, particularly showing another embodiment of a static mixing element used to facilitate mixing of the fluid components within a mixing zone.
Figure 11:
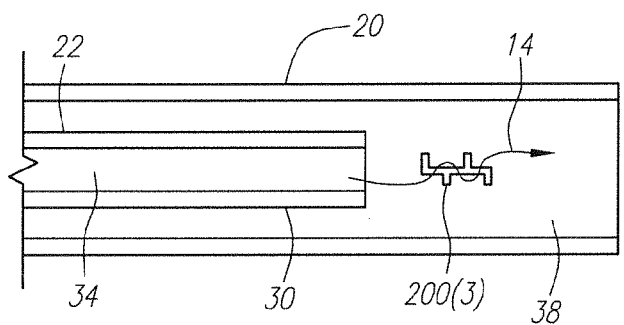
FIG. 11 is a partial cross-sectional side view of the distal end of the FIG. 1 device, particularly showing still another embodiment of a static mixing element used to facilitate mixing of the fluid components within a mixing zone.

FIGS. 9-11 illustrates several examples of how turbulent or complex flows within the mixing zone 38 may be achieved. In FIG. 9, a static mixing element 200(1) takes the form of ribs extending around the outer surface of the inner tubular element 22 in a helical arrangement. Alternatively, the mixing element 200(1) may be a coil attached to the exterior surface of the inner tubular element 22. The mixing element 200(1) induces rotational flow, as indicated by arrow 202, of the first fluid component 12 when it flows past the mixing element 200(1). Alternatively, the mixing element 200(1) may be extending from, or attached to, the interior surface of the outer tubular element 20.

FIG. 10 shows a static mixing element 200(2) at the distal end 30 of the inner tubular element 22 that is secured to, or a part of, the inner tubular element 22. The mixing element 200(2) impedes laminar flow of the second fluid component 14 as it exits the lumen 34 of the inner tubular element 22. Instead of exiting the lumen 34 of the inner tubular element 22 in a direct and laminar manner, the second fluid component 14 is diverted around the mixing element 200(2), which may be tapered to facilitate this effect.

FIG. 11 shows a static mixing element 200(3) that is secured to the interior surface of the outer tubular element 20. The mixing element 200(3) is positioned distal to the distal end 30 of the inner tubular element 22, and includes a plurality of flanges. The second fluid component 14 exits the lumen 34 of the inner tubular element 22, and it undergoes turbulent or complex flow when it encounters the mixing element 200(3).

It should be noted that the size and shape of the mixing elements 200 are not limited to those illustrated in FIGS. 9-11. Static mixing elements 200 having other configurations may also be used to improve the turbulent characteristic of the flow of either or both of the first and second fluid components.

After the first and second fluid components 12 and 14 contact and combine with each other within the mixing zone 38 (FIG. 1D), the mixture of the two fluid components is then preferably discharged out of the mixing zone 38 by fluid pressure, and into the body cavity 12. Alternatively, a pusher or a guidewire (not shown) disposed within lumen 34 of the inner tubular element 22 may be used to push out any remaining embolic composition. Also, if the inner tubular element 22 is slidably secured within the sleeve 58, as discussed previously with reference to FIG. 6, the inner tubular element 22 may be advanced distally to push out any remaining embolic composition.

The mixture of the two fluid components is preferably discharged out of the outer tubular element 20 before it partially or completely solidifies within the mixing zone 38. The discharged embolic composition then solidifies into an embolic mass for occlusion of the body cavity 12. Alternatively, the mixture of the two fluid components may partially or completely solidify within the mixing zone 38 before it is discharged out of the outer tubular element 20. The discharged embolic mass then occludes the body cavity 12.

Figure 12:
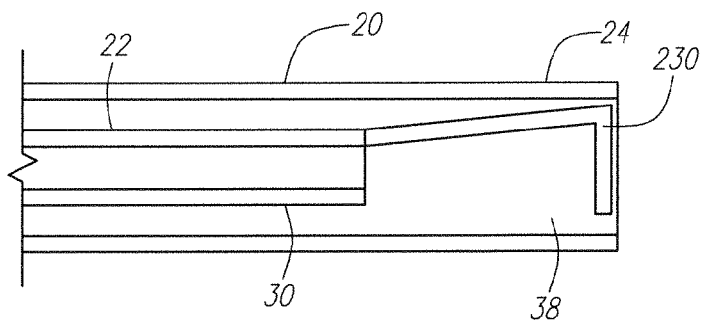
FIG. 12 is partial cross-sectional side view of the distal end of the FIG. 1 device, particularly showing one embodiment of an embolic mass cutting element.
Figure 13:
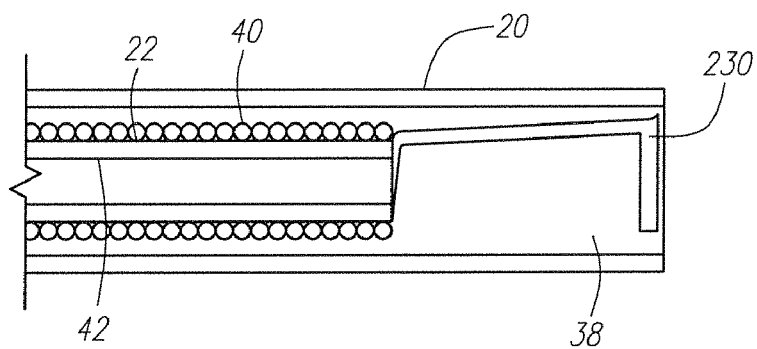
FIG. 13 is partial cross-sectional side view of the distal end of the FIG. 1 device, particularly showing another embodiment of an embolic mass cutting element.

If the combined fluid components are not completely discharged out of the device 10, some of the solidified embolic mass within the mixing zone 38 may remain attached to the solidified embolic mass outside the device 10 within the body cavity 12. FIG. 12 illustrates a cutting element 230 that may be used to cut off embolic materials at the distal end 24 of the outer tubular element 20. The cutting element 230 may be a wire, for example, connected to the distal end 30 of the inner tubular element 22. Alternatively, as illustrated in FIG. 13, if the inner tubular element 22 is reinforced with coil 40 at its distal end, the cutting element 230 may be an extension from the end of the coil 40. When the wire is turned by torquing the inner tubular element 22, the wire slices through any embolic material that extends from the distal end 24 of the outer tubular element 20.

Figure 14:
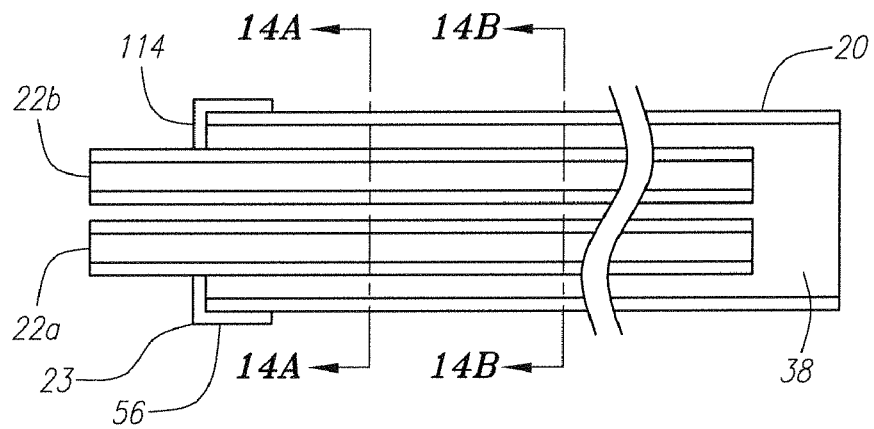
FIG. 14 is a partial cross-sectional side view of an alternative embodiment of the FIG. 1 device, particularly showing a connector having two ports for securing a first inner tubular element and a second inner tubular element in a side by side fashion.
Figure 14A:
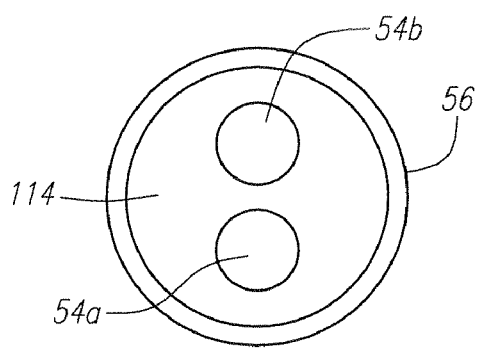
Figure 14B:
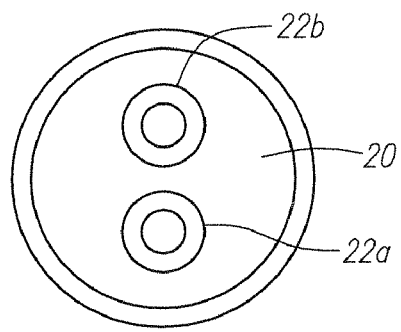

Although the embodiments above have been described in reference to delivery of fluid components by two tubular elements that are coaxial relative to each other, the scope of the invention is not so limited. For example, as shown in FIG. 14, the connector 23 may include two ports 54a and 54b for securing two inner tubular elements 22a and 22b that are positioned side by side relative to one another. The first inner tubular element 22a is for delivery of the first fluid component 12, and the second inner tubular element 22b is for delivery of the second fluid component 14. The connector 23 may also include a receiving element 56 for securing an outer tubular element 20, which serves to contain the fluid components 12 and 14 within the mixing zone 38, if it is desirable. FIG. 14A shows a sectional view of the connector 23. FIG. 14B shows a sectional view of the outer tubular element, the first inner tubular element, and the second inner tubular element.

In addition, although the embodiments above have been described in reference to delivery of two fluid components of an embolic composition, the scope of the invention, in its broadest aspects, is not so limited. The present invention also applies to delivery of fluid components of drug or medication that requires separate delivery of its components. Also, more than two tubular elements may be used when the embolic composition or medication requires separate delivery of more than two components. In such circumstances, any one or a multiple of the tubular elements may be positioned coaxially or side by side relative to another tubular element for delivery of the individual components.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. A device for delivery of a first and second fluid components through outer and inner tubular elements, respectively, each of the outer and inner tubular elements having a lumen, the device comprising:
a connector having a receiving element for detachably securing a proximal end of the outer tubular element; the receiving element having a one-piece outer flange and backing sleeve which form an annular space for receiving the proximal end of the outer tubular element; a first port being in fluid communication with the lumen of the outer tubular element when the outer tubular element is secured to the receiving element; and a second port being in fluid communication with the lumen of the inner tubular element when the inner tubular element is coaxially secured to the connector within the lumen of the outer tubular element.

2. The device of claim 1, wherein the first port is located on the receiving element.

3. The device of claim 1, wherein the first port is located at a bend adjacent to the receiving element.

4. The device of claim 1, wherein the second port is used to secure the inner tubular element to the connector.

5. The device of claim 1, wherein the connector is configured for slidably securing the inner tubular element.

6. The device of claim 1, further comprising the inner tubular element.

7. The device of claim 6, wherein the distal end of the inner tubular element includes a flexible portion.

8. The device of claim 6, further comprising a radiopaque marker adjacent the distal tip of the inner tubular element.

9. The device of claim 6, wherein the inner tubular element comprises a stopper configured for limiting proximal axial displacement of the inner tubular element relative to the connector.

10. The device of claim 6, further comprising a marker at a proximal end of the inner tubular element configured for determining the location of a distal tip of the inner tubular element relative to a distal tip of the outer tubular element.

11. The device of claim 6, further comprising a handle attached to a proximal end of the inner tubular element.

12. The device of claim 6, further comprising a cutting element connected to a distal end of the inner tubular element.

13. The device of claim 12, wherein the cutting element comprises a wire.

14. The device of claim 6, further comprising the outer tubular element.

15. The device of claim 14, further comprising a mixing zone within a distal end of the outer tubular element and outside a distal end of the inner tubular element, the mixing zone being in fluid communication with the lumens of the outer and inner tubular elements.

16. The device of claim 14, wherein the outer tubular element is a micro catheter.

17. The device of claim 14, wherein the inner and outer tubular elements each has a luminal volume selected based on a relative flow rate of the first and second fluid components.

18. The device of claim 6, further comprising a guidewire capable of being advanced through the lumen of the inner tubular element.

19. The device of claim 1, wherein the connector has luminal volumes for the first and second fluid components, respectively, the luminal volumes selected based on a relative flow rate of the first and second fluid components.

20. The device of claim 1, wherein the first and second ports are selected based on a relative flow rate of the first and second fluid components.

21. The device of claim 1, further comprising first and second supplies configured for supplying the first and second fluid components to the respective lumens of the outer and inner tubular elements.

22. A device for delivery of a first and second fluid components through a first and a second tubular elements, respectively, each of the first and the second tubular elements having a proximal end and a lumen, the device comprising:
   a connector having a first port for securing the proximal end of the first tubular element, and a second port for securing the proximal end of the second tubular element such that the second tubular element is adjacent to the first tubular element; and
   a receiving element for detachably securing a proximal end of an outer tubular element such that a distal end of the outer tubular element coaxially surrounds a distal end of the first tubular element and a distal end of the second tubular element, the receiving element having a one-piece outer flange and backing sleeve which form an annular space for receiving the proximal end of the outer tubular element.

23. The device of claim 22, the device further comprising the first and the second tubular elements.

24. The device of claim 23, the device further comprising the outer tubular element.

25. The device of claim 24, the device further comprising a mixing zone formed within the distal end of the outer tubular element and outside the distal ends of the first and the second tubular elements.

* * * * *